(12) United States Patent
Zhang et al.

(10) Patent No.: US 12,403,001 B2
(45) Date of Patent: Sep. 2, 2025

(54) LENS FOR USE IN A HUMAN OR ANIMAL BODY, AND PRODUCTION METHODS THEREOF

(71) Applicant: Agency for Science, Technology and Research, Singapore (SG)

(72) Inventors: Shuyan Zhang, Singapore (SG); Malini Olivo, Singapore (SG); Renzhe Bi, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1170 days.

(21) Appl. No.: 17/269,179

(22) PCT Filed: Aug. 16, 2019

(86) PCT No.: PCT/SG2019/050407
§ 371 (c)(1),
(2) Date: Feb. 17, 2021

(87) PCT Pub. No.: WO2020/036538
PCT Pub. Date: Feb. 20, 2020

(65) Prior Publication Data
US 2021/0275294 A1  Sep. 9, 2021

(30) Foreign Application Priority Data

Aug. 17, 2018  (SG) .......................... 10201806994W
Aug. 17, 2018  (SG) .......................... 10201806995R
Aug. 17, 2018  (SG) .......................... 10201806996P

(51) Int. Cl.
A61F 2/16  (2006.01)
G02C 7/02  (2006.01)

(52) U.S. Cl.
CPC ............ *A61F 2/1637* (2013.01); *G02C 7/022* (2013.01); *A61F 2230/0002* (2013.01); *G02C 2202/24* (2013.01)

(58) Field of Classification Search
CPC ............ A61F 2/1637; A61F 2230/0002; A61F 2210/00; G02C 7/022; G02C 2202/24;
(Continued)

(56) References Cited

U.S. PATENT DOCUMENTS

| 9,664,817 | B1 | 5/2017 | Di Falco | |
| 2012/0259411 | A1* | 10/2012 | Hong | G02C 7/049 351/159.01 |
| 2012/0314185 | A1* | 12/2012 | Bauman | G02B 1/043 977/782 |

FOREIGN PATENT DOCUMENTS

| CA | 2831640 A1 | 10/2012 |
| EP | 2778755 A1 | 9/2014 |
| WO | 2013/040047 A1 | 3/2013 |

OTHER PUBLICATIONS

Mohammadreza Khorasaninejad, Federico Capasso Metalenses: Versatile multifunctional photonic components.Science358, eaam8100(2017) (Year: 2017).*

(Continued)

*Primary Examiner* — Yashita Sharma
*Assistant Examiner* — Jose H. Trevino, III
(74) *Attorney, Agent, or Firm* — Kilpatrick Townsend & Stockton LLP

(57) ABSTRACT

There is provided a lens for use in a human or animal body, the lens comprising a metasurface configured to modulate incident light, wherein the metasurface is composed of at least one light transmissive biomaterial. Also provided is a method of making the lens.

13 Claims, 10 Drawing Sheets

(58) Field of Classification Search
CPC . G02C 7/049; A61B 1/00165; A61B 1/00174; A61B 1/00188; G02B 1/04; G02B 1/041
See application file for complete search history.

(56) References Cited

OTHER PUBLICATIONS

Fan, Zhi-Bin, et al. "Silicon nitride metalenses for close-to-one numerical aperture and wide-angle visible imaging." Physical Review Applied 10.1 (Year: 2018).*

Bae, B. J. et al., Fabrication of Moth-Eye Pattern on a Lens Using Nano Imprint Lithography and PVA Template. *Journal of the Korean Institute of Surface Engineering*, Dec. 31, 2009, vol. 42, No. 2, pp. 59-62, English Abstract Submitted.

Kamali, S. M. et al., Highly tunable elastic dielectric metasurface lenses. Laser & Photonics Reviews, Nov. 3, 2016, vol. 10, No. 6, pp. 1002-1008.

Pahlevaninezhad, H. et al., Nano-optic endoscope for high-resolution optical coherence tomography in vivo. *Nature Photonics*, Jul. 30, 2018, vol. 12, pp. 540-547.

She, A. et al., Adaptive metalenses with simultaneous electrical control of focal length, astigmatism, and shift. *Science Advances*, Feb. 23, 2018, vol. 4, No. 2, pp. eaap9957 (1-7).

Zhang, S. et al., High efficiency near diffraction-limited midinfrared flat lenses based on metasurface reflectarrays. Optics Express, Jul. 29, 2016, vol. 24, No. 16, pp. 18024-18034.

International Application No. PCT/SG2019/050407 received an International Search Report mailed Oct. 17, 2019, 6 pages.

International Application No. PCT/SG2019/050407 received Written Opinion, mailed Oct. 17, 2019, 7 pages.

\* cited by examiner

LENS FOR USE IN A HUMAN OR ANIMAL BODY, AND PRODUCTION METHODS THEREOF

TECHNICAL FIELD

Various embodiments disclosed herein relate broadly to a lens for use in human or animal body, and methods of making a lens for use in human or animal body.

BACKGROUND

In recent years, there is increasing research interest in tuning lenses to change their optical parameters (e.g. tuning optical power in response to electric signal). Different tuning mechanisms have been proposed, e.g. based on heating of phase transition materials, electrical tuning, use of microelectromechanical systems (MEMS), membrane and use of a variety of different two-dimensional (2D) materials etc. However, these studies and the eventual uses of these lenses are limited to complex optical systems.

Adapting the technologies used in complex optical systems in practical and useful biological applications, particularly in the human or animal body still present major challenges.

Biological systems are chemically complex and comprise processes that may be influenced by a large number of factors such as biomolecular interactions, temperature, pH and electric signals etc. To date, no studies has been successful in developing lens with dynamic functionality that is useful in biological systems particularly due to the complex changes occurring in the environment within the biological systems.

Moreover, most metalenses are based on inorganic materials, i.e. metals such aluminium (Al), oxides such as titanium dioxide ($TiO_2$), and semiconductors such as silicon (Si) and gallium nitride (GaN) etc, many of which are unsuitable for applications in the human or animal body.

In view of the above, there is thus a need to address or at least ameliorate one or more of the problems described above.

SUMMARY

In one aspect, there is provided a lens for use in a human or animal body, the lens comprising a metasurface configured to modulate incident light, wherein the metasurface is composed of at least one light transmissive biomaterial.

In one embodiment, the lens is substantially devoid of materials that elicit an adverse physiological response.

In one embodiment, the light transmissive biomaterial has a refractive index that is no less than about 1.33.

In one embodiment, the light transmissive biomaterial is selected from the group consisting of a hydrogel, a gelatin, a silk fibroin, a polyester, a polysiloxane, a polyacrylate, an acrylate and derivatives thereof.

In one embodiment, the polyester comprises one or more monomers selected from the group consisting of glycolic acid, glycolide, D, L-lactide, D-lactide, L-lactide, D, L-lactic acid, D-lactic acid, L-lactic acid, ε-caprolactone, trimethylene carbonate, dioxanone and p-dioxanone.

In one embodiment, the polyester is selected from the group consisting of poly(lactic-co-glycolic acid), polyglycolide, poly(glycolic acid), poly(ε-caprolactone), poly(DL-lactide-co-ε-caprolactone), poly(DL-lactide), poly(L-lactide), polylactide, poly(lactic acid), poly(lactide-co-glycolide), poly(trimethylene carbonate), polydioxanone and poly-p-dioxanone.

In one embodiment, the polysiloxane is selected from the group consisting of polydimethylsiloxane and polydimethyldiphenylsiloxane; the polyacrylate is selected from the group consisting of poly(ethyl methacrylate) and poly(ethyl acrylate); and the acrylate is selected from hydroxyethylmethacrylate (HEMA) and 2-phenylethyl methacrylate.

In one embodiment, the metasurface comprises patterned nanostructures disposed on a substrate, further wherein the patterned nanostructures and the substrate form a single monolithic piece of material.

In one embodiment, the nanostructures comprise nanopillars.

In one embodiment, the metasurface has a hyperboloidal phase profile $\varphi(r,f,\lambda)$ that is defined by the formula:

$$\varphi(r, f, \lambda) = \pm \frac{2\pi}{\lambda}\left(\sqrt{r^2 + f^2} - f\right)$$

where $\lambda$ is the wavelength, r is the radial position, f is the focal length, and the positive or negative sign is applied for diverging or converging lenses, respectively.

In one embodiment, the metasurface has a phase profile q (total) that is defined by the formulae:

$$\varphi_{total} = \varphi_{defl} + \varphi_{focus}$$

$$\varphi_{defl}(x, \lambda) = \frac{2\pi}{\lambda} \times (x) \times \sin\theta_{defl}$$

$$\varphi_{focus}(r, f, \lambda) = -\frac{2\pi}{\lambda} \times \left(\sqrt{r^2 + f^2} - f\right)$$

where $\theta_{defl}$ is the angle of incident light deflection in the x direction, r is the radial position, f is the focal length and l is the wavelength of incident light.

In one embodiment, the lens has a total thickness of from 1 micron to 1000 microns.

In one embodiment, the lens is configured to change its light modulating properties in response to changes in one or more of: chemical environment, biomolecular interactions, intensity of light, electrical and/or magnetic signals, temperature, tensile stresses, or compressive stresses.

In one embodiment, the lens is one of an intraocular lens, an endoscopic lens or an implantable deep tissue imaging enhancement lens.

In one embodiment, the lens is an intraocular lens that is adapted to be coupled to haptics and/or ciliary muscles.

In one embodiment, the lens is an endoscopic lens that is adapted to be integrated directly onto an optical fiber without an intermediate medium such as a prism for redirecting incident light thereto.

In one embodiment, the lens is an implantable lens which is part of a hybrid partially-in vivo and partially-ex vivo deep-tissue optical imaging system comprising an in vivo metasurface lens and an ex vivo microscope system with a spatial light modulator for adaptive optics.

In one aspect, there is provided a method of making a lens for use in a human or animal body, the method comprising: patterning nanostructures on a surface of a substrate to form a metasurface configured to modulate incident light, wherein the nanostructures are composed of a light transmissive biomaterial.

In one embodiment, the step of patterning nanostructures on a surface comprises configuring the nanostructure patterns such that the formed metasurface has a hyperboloidal phase profile φ(r,f,λ) or a phase profile φ(total) that is defined respectively by the following formulae:

$$\varphi(r, f, \lambda) = \pm \frac{2\pi}{\lambda}\left(\sqrt{r^2 + f^2} - f\right)$$

where λ is the wavelength, r is the radial position, f is the focal length, and the positive or negative sign is applied for diverging or converging lenses, respectively; or $$\varphi_{total} = \varphi_{defl} + \varphi_{focus}$$

$$\varphi_{defl}(x, \lambda) = \frac{2\pi}{\lambda} \times (x) \times \sin\theta_{defl}$$

$$\varphi_{focus}(r, f, \lambda) = -\frac{2\pi}{\lambda} \times \left(\sqrt{r^2 + f^2} - f\right)$$

where $\theta_{defl}$ is the angle of incident light deflection in the x direction, r is the radial position, f is the focal length and l is the wavelength of incident light.

In one embodiment, the method is performed under sterile conditions and/or further comprises a step of sterilizing the lens.

Definitions

The term "biomaterial" as used herein broadly refers to a substance that has been engineered to be suitably used in biological systems or parts of the biological systems for a medical purpose/application.

The term "biocompatible" as used herein broadly refers to a property of being compatible with biological systems or parts of the biological systems without substantially or significantly eliciting an adverse physiological response such as a toxic reaction, an immune reaction, an injury or the like. Such biological systems or parts include blood, cells, tissues, organs or the like.

The term "polymer" as used herein broadly refers to a polymeric substance composed of macromolecules with a high relative molecular mass. A polymer typically comprises repetition of a number of constitutional units. The term encompasses but is not limited to synthetic polymers and natural polymers (also known as biopolymers or biological polymers) such as polypeptides, polynucleotides and polysaccharides. Non-limiting examples of polymers include hydrogel, gelatin, silk fibroin, polyester, polysiloxane, polyacrylate and derivatives thereof.

The term "nano" as used herein is to be interpreted broadly to include dimensions in a nanoscale, i.e., the range of between about 1 nm and about 1000 nm. Accordingly, the term "nanostructures", "nanoparticles", "nanomaterials", "nanopillars" and the like as used herein may include structures that have at least one dimension in the range of no more than said range. The term "nanostructures", "nanoparticles", "nanomaterials", "nanopillars" and the like as used herein may include structures that have at least one dimension that is no more than about 1000 nm, no more than about 900 nm, no more than about 800 nm, no more than about 700 nm, no more than about 600 nm, no more than about 500 nm, no more than about 400 nm, no more than about 300 nm, no more than about 200 nm, or no more than about 100 nm, no more than about 90 nm, no more than about 80 nm, no more than about 70 nm, no more than about 60 nm, no more than about 50 nm, no more than about 40 nm, no more than about 30 nm, no more than about 20 nm, or no more than about 10 nm.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a lens for use in a human or animal body and a method of making said lens are disclosed hereinafter.

In various embodiments, the lens comprises a metasurface configured to modulate incident light. The metasurface may be composed of at least one biomaterial. The biomaterial may be one that is substantially incapable of eliciting an adverse physiological response when used in the human or animal body. The biomaterial may be a light transmissive biomaterial.

In various embodiments, the lens is an optical lens. The lens may be a synthetic lens. In various embodiments, the lens comprises a metasurface lens, or metalens. The metalens may be a concave and/or a convex lens.

In various embodiments, the incident light comprises light having wavelengths in the electromagnetic spectrum. In various embodiments, the incident light is visible light to near-infrared light having a wavelength of from about 400 nm to about 2000 nm.

In various embodiments, the biomaterial is an organo-biomaterial. In various embodiments, the biomaterial is a biomaterial comprising carbon atoms. The biomaterial may be a single molecule (such a monomer) or a polymer or a composite material that is made up of different bulk materials. The organo-biomaterial may be a hydrocarbon material.

In various embodiments, the lens is substantially devoid of or substantially free from an inorganic material or at least most of the lens does not comprise an inorganic material. In other words, in various embodiments, if the lens does contain inorganic materials for instance through the addition of inorganic additives, they do not form the majority of the lens. Accordingly, in various embodiments, the lens does not contain more than or contains less than about 10%, about 9%, about 8%, about 7%, about 6%, about 5%, about 4%, about 3%, about 2%, about 1%, or about 0.5% by weight of inorganic material. Inorganic materials may include but are not limited to metals (e.g. Au, Al), and/or oxides (e.g. $SiO_2$, $TiO_2$) and/or semiconductors (Si, GaN), and/or the like, and/or combinations thereof.

In various embodiments, the biomaterial has one or more of the following properties: bioinert, biocompatible, biodegradable and bioresorbable. In various embodiments, the biomaterial is biocompatible. Accordingly, the biomaterial may be one that is substantially incapable of eliciting an adverse physiological response such as a toxic reaction/response, an immune reaction/response, an injury or the like when used in the human or animal body. In various embodiments, the biomaterial is bioinert. Accordingly, the biomaterial may be substantially non-reactive with biological systems or parts of the biological systems such as biological blood, fluid, cells, tissues or organs. In various embodiments, the biomaterial is biodegradable. Accordingly, the biomaterial may be substantially susceptible to degradation by biological activity, for e.g. catalytic activity of enzymes. In various embodiments, biodegradation of the biomaterial involves lowering the molecular mass of the biomaterial. The biomaterial may be partially biodegradable, or fully biodegradable. In various embodiments, the biomaterial is bioresorbable. Accordingly, the biomaterial may be substantially dissolved in or absorbed by the human or animal body. The biomaterial may be partially bioresorbable, or fully bioresorbable. The biomaterial may be self-healing, self-repairing or genetically modified to fit the biological environment that it is used in.

In various embodiments, the lens is substantially devoid of materials that elicit an adverse physiological response.

In various embodiments, the metasurface is composed of at least one biomaterial. The metasurface may be composed of one, two, three, four or five different biomaterial(s). Accordingly, the metasuface may also be a composite metasurface.

In various embodiments, the biomaterial comprises organic biological materials selected from polymer-based materials, peptide-based materials, DNA-based materials, living cell sheets and composite biomaterials etc. In various embodiments therefore, the biomaterial-based metasurface disclosed herein is environmentally friendly and provides a green and sustainable strategy to making the lens for use in a human or animal body.

In various embodiments, the biomaterial has a refractive index (n) in the range of from about 1.3 to about 1.7, from about 1.31 to about 1.69, from about 1.32 to about 1.68, from about 1.33 to about 1.67, from about 1.34 to about 1.66, from about 1.35 to about 1.65, from about 1.36 to about 1.64, from about 1.37 to about 1.63, from about 1.38 to about 1.62, from about 1.39 to about 1.61, from about 1.40 to about 1.60, from about 1.41 to about 1.59, from about 1.42 to about 1.58, from about 1.43 to about 1.57, from about 1.44 to about 1.56, from about 1.45 to about 1.55, from about 1.46 to about 1.54, from about 1.47 to about 1.53, from about 1.48 to about 1.52, from about 1.49 to about 1.51 or about 1.50.

In various embodiments, the refractive index of the biomaterial is no less than about 1.7, no less than about 1.6, no less than about 1.5, no less than about 1.48, no less than about 1.46, no less than about 1.44, no less than about 1.42, no less than about 1.40, no less than about 1.38, no less than about 1.36, no less than about 1.35, no less than about 1.34, or no less than about 1.33. In various embodiments, the refractive index of the biomaterial is no less than the refractive index of water which is about 1.33 at 20° C. The biomaterial may have a refractive index that is no less than about 1.33. In various embodiments, the lowest cut-off refractive index of the biomaterial is about 1.33. It will be appreciated that, in various embodiments, the refractive index of the biomaterial is more than about 1.33, thereby creating a contrast between the ambient environment and the metasurface composing of at least one biomaterial disclosed herein. In various embodiments, the refractive index of the biomaterial is larger than the refractive index of water to provide sufficient contrast between metasurface structures and the ambient environment if the latter is made up majorly by water. Without being bound by theory, it is believed that in general, the higher the refractive index contrast is between metasurface structures and its surrounding environment, the more desirable the biomaterial is for use as an optical lens. Accordingly, in various embodiments where the lens is to be used in a biological environment, the higher the refractive index of the biomaterial, the better is the suitability of the biomaterial as a material for the metasurface disclosed herein.

In various embodiments, the biomaterial is capable of responding to external stimuli. Advantageously, embodiments of the biomaterial are capable of responding to changes in the environment (such as pH, temperature, ionic concentration, light, electric signals, electric field, magnetic field, biomolecular interactions (e.g. antibody-antigen bonding, aptamer bonding etc), solution concentration, humidity, hydration and presence of chemicals etc) for example by changing its optical or light modulating properties. In various embodiments, additive(s) is/are introduced to the light transmission biomaterial to impart desired chemical functionality to the metasurface disclosed herein. Accordingly, in various embodiments, the metasurface further comprises additives.

In various embodiments, the light transmissive biomaterial is non-opaque, translucent or substantially transparent. The light transmissive property may be such that at least about 50%, at least about 55%, at least about 60%, at least about 65%, at least about 70%, at least about 75%, at least about 80%, at least about 85%, at least about 90%, at least about 95% or to at least about 99% of light may be transmitted.

In various embodiments, the biomaterial is mechanically tunable, i.e. exhibits excellent adaptability, flexibility and/or elasticity. Advantageously, in various embodiments, the biomaterial is capable of returning from a stretched/deformed/distorted state to its original configuration upon release of a force. The biomaterial may be an elastomer.

In various embodiments, the biomaterial has a high oxygen permeability of from about 100 Dk to about 300 Dk.

In various embodiments, the biomaterial is selected from the group consisting of a hydrogel, a gelatin, a silk fibroin, a polyester, a polysiloxane, a polyacrylate, an acrylate and derivatives and combinations thereof.

In various embodiments, the biomaterial is a hydrogel comprising networks of hydrophilic and/or hydrophobic polymer chains.

In various embodiments, the hydrogel is a polyacid-based hydrogel. In one embodiment, the hydrogel comprises poly(acrylic acid), PAA having a chemical structure shown as follows:

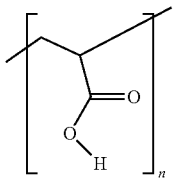

wherein n is an integer that is indicative of the degree of polymerization.

In various embodiments, the hydrogel has a refractive index (n) in the range of from about 1.37 to about 1.53, from about 1.38 to about 1.52, from about 1.39 to about 1.51, from about 1.40 to about 1.50, from about 1.41 to about 1.49, from about 1.42 to about 1.48, from about 1.43 to about 1.47, from about 1.44 to about 1.46, or about 1.45.

In various embodiments, the higher the refractive index of the hydrogel, the better is the suitability of the hydrogel as a material for the metasurface disclosed herein.

In various embodiments, the refractive index of the hydrogel is no less than the refractive index of water which is about 1.33 at 20° C. In various embodiments therefore, the lowest cut-off refractive index of the hydrogel is about 1.33.

In various embodiments, the hydrogel is selected from any one of a temperature-responsive hydrogel, pH-responsive hydrogel, light-responsive hydrogel, electro-responsive hydrogel, magnetic-responsive hydrogel, ionic-responsive hydrogel and multi-responsive hydrogel. In various embodiments, stimuli-responsive monomers/co-monomers are incorporated into the backbone of the polymer network or pendant groups within the hydrogel to obtain hydrogels that are tunable and responsive to one or more different stimuli.

In various embodiments, the hydrogel is a temperature-responsive/temperature-dependent/thermo-sensitive hydrogel that comprises one or more polymers selected from the group consisting of poly(N-isopropylacrylamide) (PNIPAM), poly(N,N-diethylacrylamide) (PDEAM), poly (methyl vinyl ether) (PMVE), polyvinyl chloride (PVC), pluronic, tetronic, gelan gum, methylcellulose, hydroxypropyl methylcellulose, chitosan, poly(acrylic acid) (PAA), polyacrylamide (PAAm).

In various embodiments, the hydrogel is a temperature-responsive hydrogel that is capable of changing its structural properties in response to the temperature of the environment. In various embodiments, the temperature-responsive hydrogel undergoes a reversible transition between a swollen state and a collapsed state with changes in temperature. The temperature-responsive hydrogel may be an inverse temperature-dependent hydrogel or a positive temperature-dependent hydrogel. When temperature increases, an inverse temperature-dependent hydrogel typically contracts while a positive temperature-dependent hydrogel typically swells. In various embodiments, an inverse temperature-dependent hydrogel comprises polymer chains that contain moderately hydrophobic groups or a mixture of hydrophilic and hydrophobic segments. In one embodiment, the inverse temperature-dependent hydrogel comprises poly(N-isopropylacrylamide) (PNIPAm). In various embodiments, a positive temperature-dependent hydrogel comprises polymer networks made up of poly(acrylic acid) (PAA) and polyacrylamide (PAAm). In various embodiments, temperature-responsive hydrogel may be prepared starting from poloxamers comprising poly(ethylene oxide)-b-poly(propylene oxide)-b-poly(ethylene oxide) (Pluronics®, Tetronics®) poloxamer).

In various embodiments, the hydrogel is a pH-responsive/pH-sensitive hydrogel that comprises chitosan, polyacids and/or polybases. The polyacids may be selected from the group consisting of poly(acrylic acid) (PAA), poly(methacrylic acid) (PMAA) and poly(2-ethyl acrylic acid) (PEAA). The polybases may be selected from the group consisting of poly(N,N-dimethylaminoethyl methacrylate) (PDMAEMA), poly(N,N-diethyl aminoethyl methacrylate) (PDEAEMA) and poly(4-vinylpyridine) (P4VP).

In various embodiments, the hydrogel is a pH-responsive hydrogel that is capable of changing its structural properties in response to the pH of the environment. In various embodiments, the pH-responsive hydrogel comprises hydrophilic networks that undergo volume deformations with changes in pH. For example, when pH increases, embodiments of a pH-responsive hydrogel lose a hydrogen ion (i.e. $H^+$) and imbibe water as osmotic pressure increases. In various embodiments, pH-sensitive polymers possess ionizable functional groups (such as —COOH and —OH groups) which accepts or releases protons in response to changes in the environmental pH. The pH-sensitive polymers may be selected from the group consisting of poly(acrylic acid) and chitosan.

In various embodiments, the hydrogel is a light-responsive hydrogel that is capable of changing its physical and/or chemical properties such as elasticity, viscosity, shape and swelling degree etc. upon light irradiation. In various embodiments, the light-responsive hydrogel comprises polymeric network that possesses light reactive groups such as photochromic moieties. In some embodiments, light-sensitive chromophores such as azobenzenes are added into a hydrogel network, thereby making embodiments of the hydrogel sensitive to UV light. In some embodiments, photocleavable groups are immobilized into a hydrogel network, thereby making embodiments of the hydrogel sensitive to UV light. In other embodiments, chlorophyllin chromophore is introduced into a hydrogel, e.g. a poly(N-isopropylacrylamide) (PNIPAM)-based hydrogel, so that it becomes sensitive to visible light. In other embodiments, up-conversion nanoparticles with multiphoton effect are introduced into a hydrogel so that near-infrared light can be used to trigger the structural change.

In various embodiments, the hydrogel is an electro-responsive hydrogel that is capable of expanding, contracting, elongating and bending under the influence of an electric field/in response to electrical signals, for e.g. generated by the human or animal body provided by the human nervous system. As will be appreciated, the changes in the physical/structural properties depend on the hydrogel shape and its position relative to the electrodes. In various embodiments, the electro-responsive hydrogel comprises polymers selected from the group consisting of naturally occurring polymers and synthetic polymers. Naturally occurring polymers may include hyaluronic acid, chondroitin sulfate or a polysaccharide such as agarose. Synthetic polymers may include (meth)acrylate based polymers synthesized by crosslinking polyionic chains. In various embodiments, the electro-responsive hydrogel comprises conducting polymers.

In various embodiments, the hydrogel is a magnetic-responsive hydrogel that is capable of expanding, contracting, elongating and bending under the influence of a magnetic field. In various embodiments, the electro-responsive hydrogel comprises magnetic particles that allow embodiments of the hydrogel to deform under the influence of an externally applied magnetic field. In some embodiments, magnetic iron oxide nanoparticles (MIONs) or also known as super magnetic iron oxide nanoparticles (SPIONs) are incorporated into a polymer matrix, which can transform electromagnetic energy into heat. In various embodiments therefore, a magnetic-responsive hydrogel acts as a thermo-responsive hydrogel.

In various embodiments, the hydrogel is an ionic-responsive hydrogel that is capable of undergoing relatively large and abrupt physical and/or chemical changes in response to small changes in the ion concentration of the environment. In various embodiments, the ionic-responsive hydrogel comprises a polymer containing acrylate and acrylic acid chains. In one embodiment, the ionic-responsive hydrogel comprises poly(N,N-dimethylaminoethyl methacrylate-co-acrylic acid) copolymer.

In various embodiments, the hydrogel is a multi-responsive hydrogel that is capable of responding to two or more external stimuli. In various embodiments, the multi-responsive hydrogel is a copolymer displaying at least two sensitivities.

In one embodiment, the multi-responsive hydrogel comprises a triblock copolymer poly(amidoamine)-poly(ethylene glycol)-poly(amidoamine) (PAA-PEG-PAA), which may be obtained by conjugating PAA to PEG via Michael addition polymerization.

In various embodiments, the biomaterial is a gelatin comprising networks of polypeptide chains. In various embodiments, the gelatin comprises from about 50 to about 4,000 amino acids. An example of a structural unit present in gelatin which comprises amino acids selected from the group consisting of alanine (Ala), glycine (Gly), proline (Pro), arginine (Arg), glutamic acid (Glu), hydroxyproline (Hyp) is shown as follows:

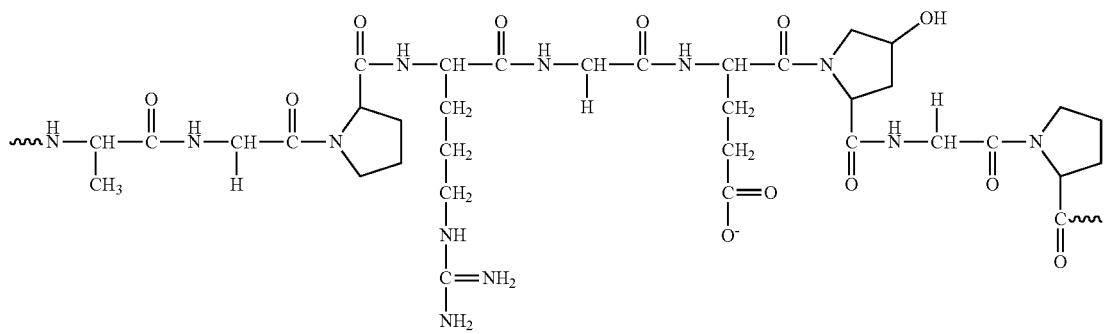

In various embodiments, the gelatin has a refractive index (n) in the range of from about 1.51 to about 1.54. The gelatin may have a refractive index (n) of about 1.51, about 1.52, about 1.53 or about 1.54.

In various embodiments, the higher the refractive index of the gelatin, the better is the suitability of the gelatin as a material for the metasurface disclosed herein.

In various embodiments, the refractive index of the gelatin is no less than the refractive index of water which is about 1.33 at 20° C. In various embodiments therefore, the lowest cut-off refractive index of the gelatin is about 1.33.

In various embodiments, the biomaterial is a silk fibroin comprising networks of polypeptide chains. An example of a structural unit present in silk fibroin which comprises amino acids selected from the group consisting of alanine (Ala), glycine (Gly) and glycylalanine (Gly-Ala) is shown as follows:

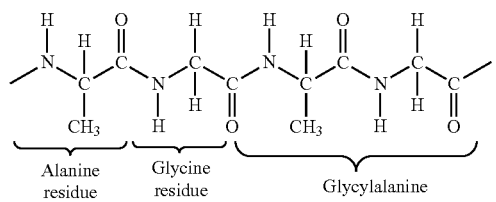

In various embodiments, the silk fibroin has a refractive index (n) of about 1.55.

In various embodiments, the higher the refractive index of the silk fibroin, the better is the suitability of the silk fibroin as a material for the metasurface disclosed herein.

In various embodiments, the refractive index of the silk fibroin is no less than the refractive index of water which is about 1.33 at 20° C. In various embodiments therefore, the lowest cut-off refractive index of the silk fibroin is about 1.33.

In various embodiments, the biomaterial is a polyester. In various embodiments, the polyester comprises one or more monomers selected from the group consisting of glycolic acid, glycolide, D, L-lactide, D-lactide, L-lactide, D, L-lactic acid, D-lactic acid, L-lactic acid, ε-caprolactone, trimethylene carbonate and dioxanone. The polyester may be a homopolymer (i.e. polymer comprising a single type of repeating unit) or a copolymer (i.e. polymer comprising two or more types of repeating units) such as a bipolymer, terpolymer or quaterpolymer. As may be appreciated, the monomers may be added in a variety of different compositions, depending on the desired functionality to be achieved.

In various embodiments, the polyester is a homopolymer selected from the group consisting of polyglycolide, poly(glycolic acid), poly(ε-caprolactone), poly(DL-lactide) or PDLA, poly(L-lactide) or PLLA, polylactide, poly(lactic acid), poly(trimethylene carbonate), polydioxanone (PDO) and poly-p-dioxanone (PDS).

In various embodiments, the polyester is a copolymer selected from the group consisting of poly(lactic-co-glycolic acid), poly(DL-lactide-co-ε-caprolactone) or DL-PLCLs and poly(lactide-co-glycolide). In various embodiments, when the copolymer is made up of two different types of monomers (i.e. monomer 1 and monomer 2), monomer 1 and monomer 2 are added at a ratio of from about 15:85 to about 85:15. In some embodiments, monomer 1 and monomer 2 are added at a ratio of about 50:50.

TABLE 1

Chemical Structure of Exemplary Polyesters

| Exemplary Polyester | Chemical Structure |
| --- | --- |
| poly(lactic-co-glycolic acid) PLGA or PLG | 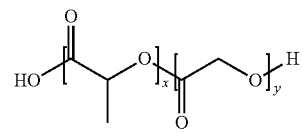 |
| polyglycolide or poly(glycolic acid) PGA | 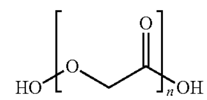 |
| poly(ε-caprolactone) PCL | 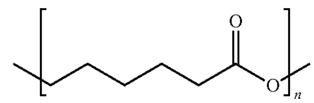 |
| polylactide or poly(lactic acid) PLA | 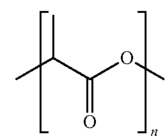 |
| poly(trimethylene carbonate) PTMC | 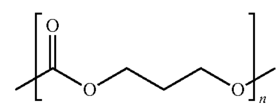 |
| poly-p-dioxanone PDS | | x, y and n are integers that are indicative of the degree of polymerization

In various embodiments, the biomaterial is a silicone or polysiloxane. In various embodiments, the polysiloxane comprises alternating Si and O atoms, i.e. —Si—O—Si— linkages. In various embodiments, the polysiloxane is flexible. The polysiloxane may be selected from the group consisting of polydimethylsiloxane (PDMS) and polydimethyldiphenylsiloxane (PDMDPS).

In one embodiment, the polysiloxane is polydimethylsiloxane (PDMS) having a chemical structure shown as follows:

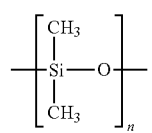

wherein n is an integer that is indicative of the degree of polymerization.

In one embodiment, the polysiloxane is polydimethyldiphenylsiloxane (PDMDPS) having a chemical structure shown as follows:

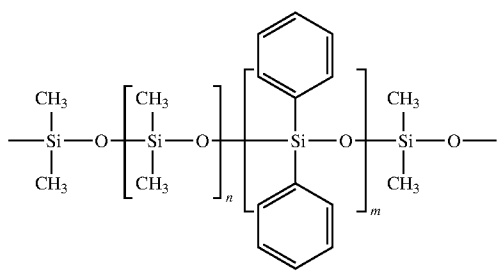

wherein n and m are integers that are indicative of the degree of polymerization.

In various embodiments, the biomaterial is an acrylic or polyacrylate. In various embodiments, the polyacrylate is flexible. In various embodiments, the polyacrylate comprises one or more monomers selected from the group consisting of acrylic acid, methacrylic acid and derivatives thereof. The acrylic acid derivative thereof may comprise esters of acrylic acid such as methyl acrylate, ethyl acrylate, butyl acrylate and 2-ethylhexyl acrylate (2EHA). The methacrylic acid derivative thereof may comprise esters of methacrylic acid such as methyl methacrylate (MMA), ethyl methacrylate (EMA) and hydroxyethyl methacrylate (HEMA). The polysiloxane may be selected from the group consisting of poly(ethyl methacrylate) (PEMA) and poly(ethyl acrylate) (PEA).

In various embodiments, the biomaterial comprises an acrylate. In various embodiments, the acrylate is flexible. The acrylate may be selected from the group consisting of hydroxyethylmethacrylate (HEMA) and 2-phenylethyl methacrylate.

In one embodiment, the acrylate is hydroxyethylmethacrylate (HEMA) having a chemical structure shown as follows:

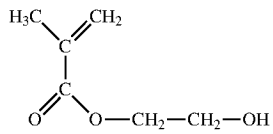

In one embodiment, the acrylate is 2-phenylethyl methacrylate having a chemical structure shown as follows:

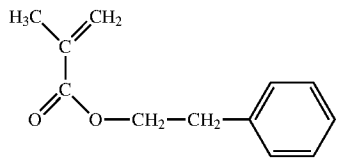

In various embodiments, the metasurface comprises patterned nanostructures disposed (or placed) on a substrate. In various embodiments, the patterned nanostructures and the substrate form a single monolithic piece of material. The nanostructures may serve as one or more of fixed optical phase shifters, amplitude modulators, and/or polarizing changing elements, optionally in an array to thereby control the wavefront of light. Accordingly, in various embodiments, the nanostructures are patterned based on a desired spatial distribution to allow a desired outcome of optical phases, amplitudes, and/or polarization of light to be effected by the lens. In various embodiments therefore, the lens has one or more of the following functionalities: adjustable lenses, beam steering gratings, higher-order wavefront aberration correctors, structural color generators, lenses axicons, blazed gratings, vortex plates and/or wave plates.

In various embodiments, the nanostructures are spaced less than the distance corresponding to the wavelength of the incident light e.g. subwavelength spacing. In various embodiments, the nanostructures arrangement are similar to or correspond substantially to the arrangements shown in FIG. 10 and/or FIG. 13. Advantageously, by reducing the spacing of these metasurface elements/nanostructures, diffraction orders can be suppressed, thus improving performance, and in particular, efficiency of the metasurface device.

In various embodiments, at least one light transmissive biomaterial comprises at least one of the nanostructures or the substrate. In one embodiment, both the nanostructures and substrate are light transmissive. In another embodiment, the substrate is light transmissive while the nanostructures are not light transmissive. The nanostructures and/or substrate may be composed of one or more of the biomaterials disclosed herein.

In various embodiments, the nanostructures comprise nanopillars. It will be appreciated that other nanostructures may also be applied to impart the desired optical properties to the metasurface. For example, nano-fins, nano-pyramids, nano-discs or the like may also be introduced as appropriate.

In various embodiments, the metasurface lens has a hyperboloidal phase profile $\varphi(r,f,\lambda)$ that is defined by the formula:

$$\varphi(r, f, \lambda) = \pm \frac{2\pi}{\lambda}\left(\sqrt{r^2 + f^2} - f\right)$$

where $\lambda$ is the wavelength, r is the radial position, f is the focal length, and the positive or negative sign is applied for diverging or converging lenses, respectively.

In various embodiments, the metasurface has a phase profile q (total) that is defined by the formulae:

$$\varphi_{total} = \varphi_{defl} + \varphi_{focus}$$

$$\varphi_{defl}(x, \lambda) = \frac{2\pi}{\lambda} \times (x) \times \sin\theta_{defl}$$

$$\varphi_{focus}(r, f, \lambda) = -\frac{2\pi}{\lambda} \times \left(\sqrt{r^2 + f^2} - f\right)$$

where $\theta_{defl}$ is the angle of incident light deflection in the x direction, r is the radial position, f is the focal length and l is the wavelength of incident light.

In various embodiments, $\theta_{defl}$ has a value of from about 0° to about 45°, from about 0° to about 20°, or from about 0° to about 10°. In various embodiments, $\theta_{defl}$ has a value of about 0°, about 5°, or about 10°.

In various embodiments, the lens has a thickness, optionally a total thickness, of from about 1 micron to about 1000 microns, from about 10 microns to about 500 microns, from about 30 microns to about 300 microns, from about 50 microns to about 100 microns, from about 55 microns to about 95 microns, from about 60 microns to about 90 microns, from about 65 microns to about 85 microns, from about 70 microns to about 80 microns or about 75 microns.

In various embodiments, the lens is configured to change its light modulating properties in response to changes in one or more of: chemical environment, biomolecular interactions (e.g. antibody-antigen bonding or aptamer bonding), intensity of light, electrical signals, magnetic signals, temperature, tensile stresses, or compressive stresses.

In various embodiments, the lens is suitable for use in medical applications where contact or possible contact with the human/animal body is foreseeable, for example as an implant.

In various embodiments, the lens is one of an intraocular lens, an endoscopic lens or an implantable deep tissue imaging enhancement lens.

In various embodiments, the lens is an intraocular lens that is adapted to be coupled to haptics and/or ciliary muscles. The intraocular lens may be non-tunable or tunable.

In various embodiments, a biomaterial suitable for use in making intraocular lens is one that has one or more of the following properties: biocompatible, hydrophilic and has a high oxygen permeability e.g. above 100Dk. In various embodiments, a biomaterial suitable for use in making a tunable intraocular lens is one that has one or more of the following properties: biocompatible, hydrophilic, has a high oxygen permeability e.g. above 100Dk and mechanically tunable (i.e. flexible). Examples of a biomaterial suitable for use in making a tunable intraocular lens are hydrogel, silicone or polysiloxane and acrylic or polyacrylate. In one embodiment, tunable intraocular lens comprises hydrogel as the light transmissive biomaterial.

In various embodiments, the lens is an endoscopic lens that is adapted to be integrated directly onto an optical fiber without an intermediate medium such as a prism for redirecting incident light thereto.

In various embodiments, the lens is an implantable lens which is part of a hybrid partially-in vivo and partially-ex vivo deep-tissue optical imaging system comprising an in vivo metasurface lens and an ex vivo microscope system with a spatial light modulator for adaptive optics.

In various embodiments, there is provided an endoscope comprising a lens disclosed herein coupled/integrated onto an optical fiber and a light source adapted to direct incident light to said lens, wherein said lens focuses incident light from the light source into/to the core of the optical fiber for transmission of the light signal therethrough.

In various embodiments, a biomaterial suitable for use in making an endoscopic lens is one that has one or more of the following properties: biocompatible and bioinert. An example of a light transmissive biomaterial suitable for use in making an endoscopic lens is hydrogel.

In various embodiments, the lens is an implantable deep tissue imaging enhancement lens.

In various embodiments, a biomaterial suitable for use in making an implantable deep tissue imaging enhancement lens is one that has one or more of the following properties: biocompatible and bioinert. An example of a light transmissive biomaterial suitable for use in making an endoscopic lens is hydrogel.

In various embodiments, there is provided a method of making a lens for use in a human or animal body, the method comprising: patterning nanostructures on a surface of a substrate to form a metasurface configured to modulate incident light, wherein the nanostructures are composed of a biomaterial. The biomaterial may be one that is substantially incapable of eliciting an adverse physiological response when used in the human or animal body.

In various embodiments, the step of patterning nanostructures on a surface of a substrate comprises any one of the processes selected from the group consisting of templating/nano-imprint lithography, self-assembly and 3D printing (additive manufacturing). The substrate may be selected from silicon dioxide ($SiO_2$), silicon nitride ($Si_3N_4$), metals and photoresists.

In various embodiments, the method of making a lens for use in a human or animal body is performed under sterile conditions and/or further comprises a step of sterilizing the lens. In various embodiments, additional steps are taken to ensure that one or more of the following infections: bacterial, viral, fungal, parasitic and prion infections are prevented. In various embodiments, the step of sterilizing the lens is performed in a sterile environment. The sterilization process may comprise adding any one of the following solutions: multipurpose solutions including anti-bio formulations such as chlorhexidine, hydrogen peroxide-based solutions, saline and enzymatic protein removers to the lens/metasurface/light transmissive material.

In various embodiments, there is provided a method of performing visual correction in a subject, the method comprising replacing or overlaying the natural lens of the subject or a portion thereof with the lens as disclosed herein. In various embodiments, the replacing or overlaying step comprises injecting the lens into a capsular bag of the subject's eye. In various embodiments, the replacing or overlaying step further comprises making an excision in the subject's eye prior to injection. Pre-measurements of the subject's eye or the natural lens may be made to determine the suitable dimensions of the lens for injection. In various embodiments, the visual correction comprises one or more of a defocus aberration correction, an astigmatism aberration correction and a shift aberration correction. The lens may be a single-piece intraocular lens/one-piece intraocular lens or a three-piece intraocular lens. The lens may also be coupled to haptics. The haptics may be loop haptics (e.g. C-loops, J loops, closed loops etc.) or plate haptics. Furthermore, the lens may be foldable.

In various embodiments, the replacing or overlaying step comprises attaching the lens to a ciliary zonule of the subject's eye. In some embodiments, the attaching step comprises gluing, e.g. by use of surgical glue, the lens to the ciliary zonule. In some embodiments, the attaching step comprises welding the lens to the ciliary zonule or to glycoprotein fibrillin contained in the ciliary zonule, for example, by use of a laser. In some embodiments, the attaching step comprises mechanically securing the lens to the ciliary zonule, for example, by use of small hook fasteners.

In various embodiments, there is provided a method of treating an ocular disorder in a subject, the method comprising replacing or overlaying the natural lens of the subject or a portion thereof with the lens as disclosed herein. In various embodiments, the ocular disorder is selected from the group consisting of: myopia, hyperopia, astigmatism, cataract, macular degeneration, age-related macular degeneration and combinations thereof. In various embodiments, the method further comprises measuring the corneal curvature and/or the axial length of the subject's eye to determine the refractive error prior to the replacing or overlaying step. In various embodiments, the lens is configured to correct for the refractive error.

In various embodiments, there is provided a method for imaging in deep tissue or imaging in a scattering media, the method comprising implanting one or more of the lenses as disclosed herein into the tissue or media. In various embodiments, one lens, two lenses, three lenses, four lenses or five lenses may be implanted. In some embodiments, all of the lenses are substantially identical. In some embodiments, one or more of the lens are different. In some embodiments, all of the lenses are different. In various embodiments, the one or more lens has a thickness of from about 30 μm to about 120 μm or from about 50 μm to about 100 μm. In various embodiments, the one or more lens has a thickness of about 30 μm, about 40 μm, about 50 μm, about 60 μm, about 70 μm, about 80 μm, about 90 μm, about 100 μm, about 110 μm or about 120 μm.

In various embodiments, one or more lenses are implanted at different depths within the tissue or media. The one or more lenses may further be substantially aligned along an optical axis. In various embodiments, the distance between two lenses is from about 0.1 mm to about 12 mm, or from about 2 mm to about 10 mm (or 1 cm). In various embodiments, the distance between two lenses is about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, about 11 mm, about 11.5 mm or about 12 mm. In various embodiments, the focal length of the one or more lens is from about 0.5 mm to about 12 mm, or from about 2 mm to about 10 mm (or 1 cm). In various embodiments, the focal length of the one or more lens is about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, about 11 mm, about 11.5 mm or about 12 mm. Depending on the absorption of the tissue or the scattering media, the distance between the two lenses or the focal length may vary.

In various embodiments, the method further comprises providing a light source e.g. a laser source and one or more optical components for modulating the light source e.g. a spatial light modulator (SLM) and/or a microscope objective for delivering light/modulated light to the one or more lens.

In one embodiment, the method comprises a method for imaging a brain tissue. In various embodiments, the method further comprises removing a portion of the subject's scalp/skin and/or skull prior to the implanting step.

In various embodiments, there is provided a system for imaging in deep tissue or imaging in a scattering media, the system comprising: a light source for delivering light into the tissue or media, and one or more lens for implanting into the tissue or media to focus light on an image plane within the tissue or media. In some embodiments, the system may further comprise one or more optical components for modulating the light source before delivery into the tissue or media.

EXAMPLES

Figure 1:
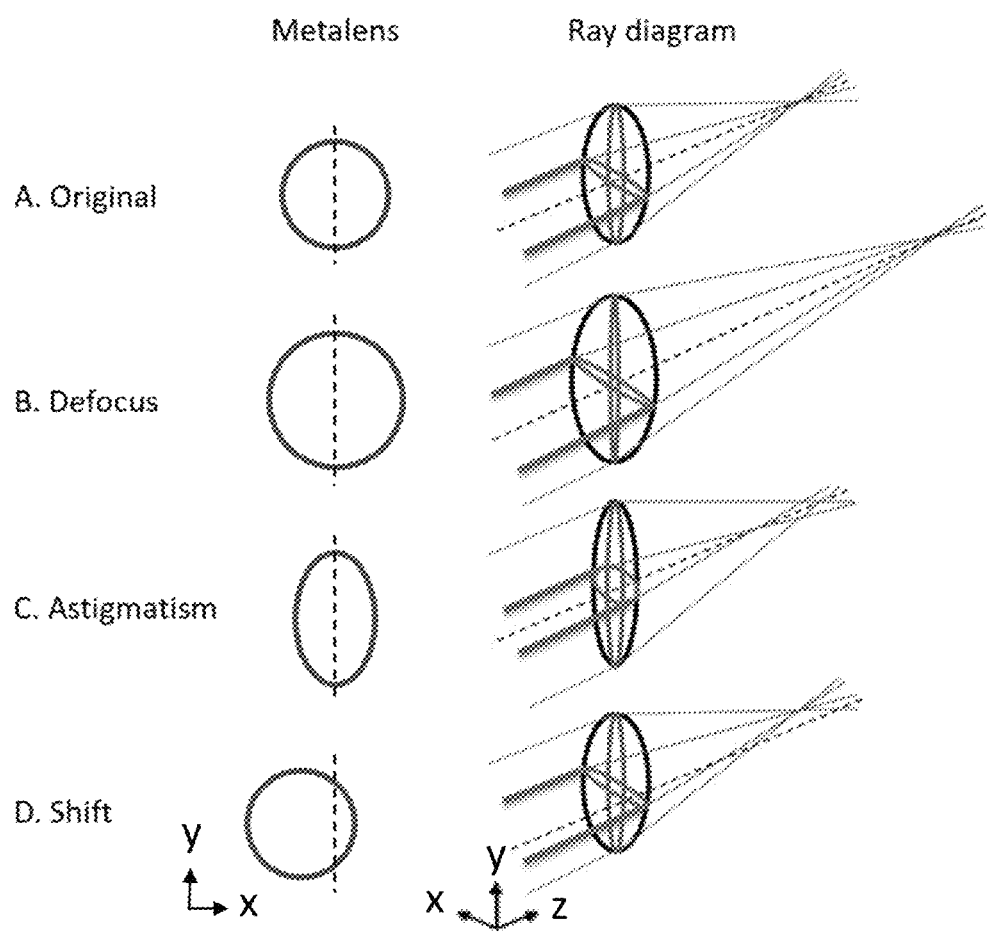
FIG. 1 is an illustration of focal length, astigmatism, and shift of a biomaterial-based metalens being tuned by controlling and changing the shape of the metalens in accordance with various embodiments disclosed herein.

Example embodiments of the disclosure will be better understood and readily apparent to one of ordinary skill in the art from the following examples, tables and if applicable, in conjunction with the figures. It should be appreciated that other modifications related to structural, electrical and optical changes may be made without deviating from the scope of the invention. Example embodiments are not necessarily mutually exclusive as some may be combined with one or more embodiments to form new example embodiments. The example embodiments should not be construed as limiting the scope of the disclosure.

Example 1: Fabrication of a Biomaterial-Based Metasurface

The biomaterial-based metasurface in accordance with various embodiments disclosed herein may be fabricated using different techniques including templating/nano-imprint lithography, self-assembly, and 3D printing. The details of each of these techniques adapted to produce embodiments of the biomaterial-based metasurface disclosed herein are discussed as follows.

Example 1.1: Templating/Nano-Imprint Lithography i. Preparation of Master/Template Mold The master material can be SiO2, Si3N4, metals or photoresists. The master mold is fabricated with the negative of the metasurface patterns having nanostructures with subwavelength spacing placed on a substrate according to a designed phase profile, e.g. in FIG. 10 and FIG. 13 using any of the following high resolution patterning techniques: photolithography, e-beam lithography or focused-ion beam. Dry or wet etching may be employed during processing. Depending on the choice of master material, the etchant, temperature and environmental conditions etc. employed may vary. The final master mold containing the negative of the metasurface patterns with subwavelength features may be reused.

ii. Casting

A liquid mixture comprising a biomaterial base (e.g. a hydrogel) and a catalyst or a curing agent (e.g. a mixture of a platinum complex and copolymers of methylhydrosiloxane and dimethylsiloxane from Dow Corning) is poured over the master mold. The liquid mixture is then cured by heating to elevated temperatures (e.g. between 5° and 150° C.) until the mixture solidifies. Depending on the material of the cast, the mold may or may not be coated with a mold release layer, such as a thermal release adhesive or a chemical release adhesive. It will be appreciated that any catalysts or curing agents that are suitable for the biomaterial base and commercially available may be used.

iii. Release

After cooling down, the biomaterial-based solidified mixture is peeled off from the master mold. If a mold release layer is present, debinding of the layer is carried out using the appropriate mechanism e.g. by use of heat or chemical, before peeling off. The metasurface patterns are now transferred to the biomaterial.

Example 1.2: Self-Assembly

The master material can be $SiO_2$, Si, metals. The master mold is fabricated with the positive of the metasurface patterns having nanostructures with subwavelength spacing placed on a substrate according to a designed phase profile, e.g. in FIG. 10 and FIG. 13 using any of the following high resolution patterning techniques: photolithography, e-beam lithography or focused-ion beam. The master mold is then functionalised with self-assembly components e.g. atoms, molecules, lipids and proteins. In one example, the master mold is functionalised with hydrogel which self-assemble by establishing supramolecular interacts such as ionic bonds, weak physical entanglements and hydrogen bonds. The final master mold containing the positive of the metasurface patterns with subwavelength features may be reused.

Example 1.3: 3D Printing (Additive Manufacturing)

Figure 10:
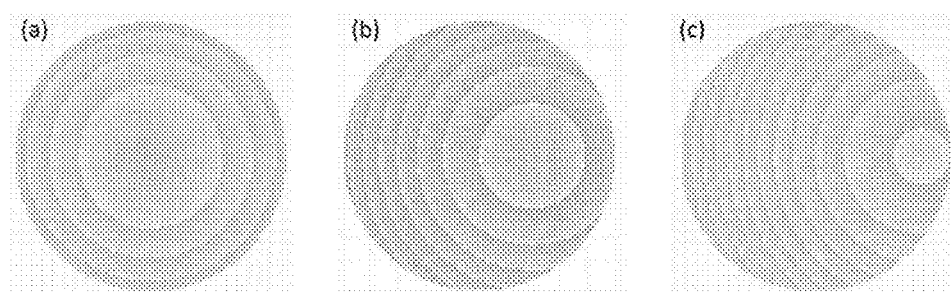
FIG. 10 shows the biomaterial-based metasurface designs for (a) normal-view endoscope; (b) 5° side-view endoscope and (c) 10° side-view endoscope in accordance with various embodiments disclosed herein. Each dot is a metasurface structure based on the metasurface phase profile.
Figure 13:
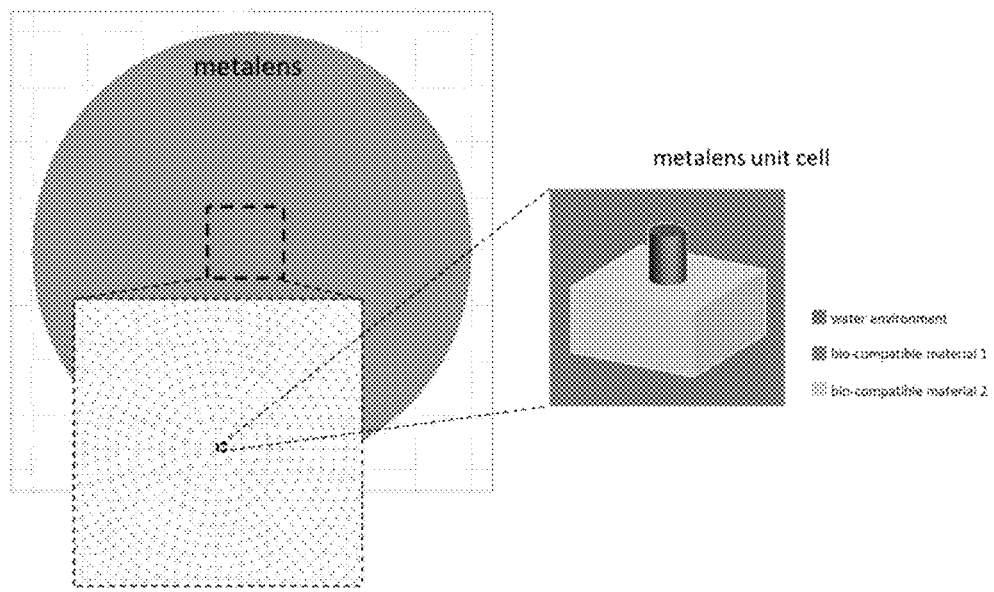
FIG. 13 is a schematic diagram of bio-compatible metalens design in accordance with various embodiments disclosed herein. In the diagram, each circle represents a pillar structure made of bio-compatible materials.

The metasurface patterns having nanostructures with subwavelength spacing placed on a substrate according to a designed phase profile, e.g. in FIG. 10 and FIG. 13 are directly written on biomaterials through multiphoton (such as 2 photon) absorption polymerization. A laser, eg. an ultrafast laser source such as a femtosecond laser, is used to trigger a chemical reaction that causes polymerization of a photosensitive monomer and it scans the monomer mixture in 3D to generate the 3D pattern structures.

Example 2: Principles of Focal Length, Astigmatism, and Shift Tuning Through Metalenses In accordance with various embodiments disclosed herein, a biomaterial-based metasurface lens is constructed by a metasurface to fulfil the following hyperboloidal phase profile, $$\varphi(r, f, \lambda) = \pm \frac{2\pi}{\lambda}\left(\sqrt{r^2 + f^2} - f\right)$$

where $\lambda$ is the wavelength of incident light, r is the radial position, f is the focal length, and the positive or negative sign is applied for diverging or converging lenses, respectively. Such lens having a hyperboloidal phase profile according to the above equation focuses light that is free of spherical aberrations for normal incidence (infinity-corrected) illumination.

By changing or controlling the shape of a metasurface lens (metalens), the focal length, astigmatism, and shift can be tuned accordingly (see FIG. 1A-D). The wavefront generated by the metalens determines the subsequent beam shaping. For example, the focal length can be increased by enlarging the metalens area (e.g. by pulling on the metalens to produce a uniform and isotropic stretch) and the focal length can be decreased by shrinking the metalens area (e.g. by pushing on the metalens). For astigmatism aberration, the metalens shape can be made elliptical (e.g. by a combination of horizontal and vertical pushes and pulls to produce an asymmetric stretch) so that the focal spot is shifted. For shift aberration, the position of the metalens in the plane can be shifted (e.g. by lateral push or pull to produce a lateral displacement in the x,y plane) so that the focal spot is shifted.

Figure 2:
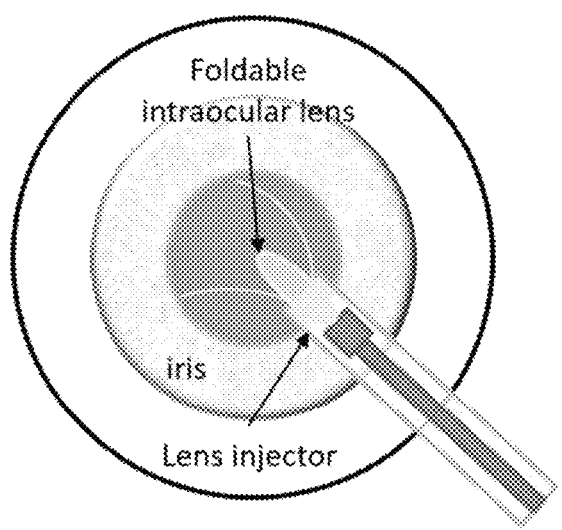
FIG. 2 is a schematic diagram of a method of inserting a metasurface-based intraocular lens (IOL) into an eye through a lens injector in accordance with an example embodiment as disclosed herein.

Example 3: Fabrication of Tunable and Non-Tunable Metasurface Lens (Metalens) Based Ultrathin (Micron) Intraocular Lens (IOL) for In Vivo Implantation The biomaterial-based metasurface lens may be applied as an intraocular lens (IOL) in accordance with various embodiments disclosed herein. For an implantable meta-IOL, support structures including flexure-based frames, foldable support structures and haptics (e.g. C-loop/plate haptics), are designed and fabricated to produce a foldable meta-IOL. The foldable meta-IOL can then be deployed inside the eye by needle injection through a small incision into the capsular bag and then allowed to unfold (e.g. using standard surgical procedures or the more advanced procedures) (see FIG. 2). The support structures may be integrally formed with a metalens, or separately fabricated and subsequently attached to a pre-formed metalens using known techniques.

Figure 3:
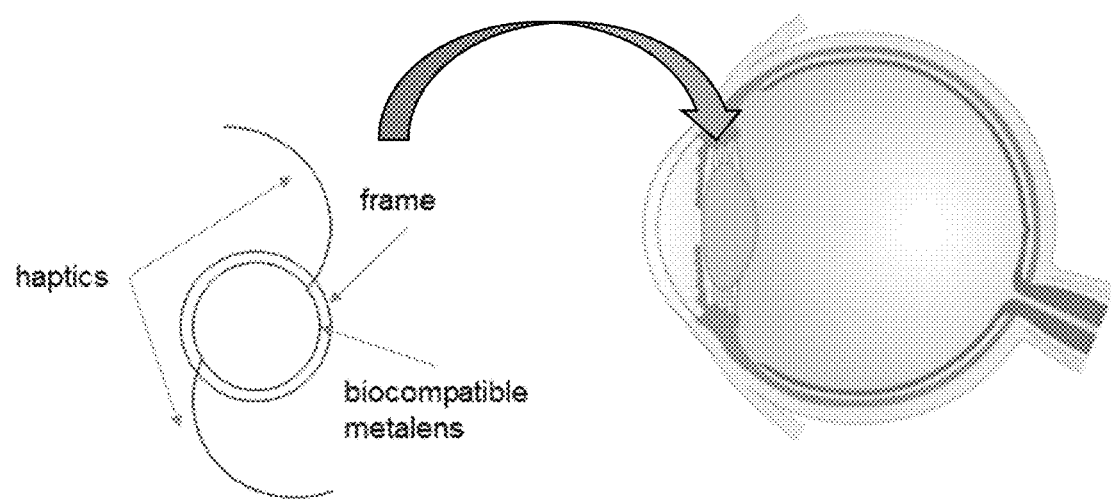
FIG. 3 is a schematic diagram of a non-tunable bio-metalens based ultrathin IOL for in vivo implantation in accordance with an example embodiment as disclosed herein.

For a non-tunable biomaterial-based metasurface IOL, a flexible IOL is supported and held in place using support structures in the form of haptics (see FIG. 3).

Figure 4:
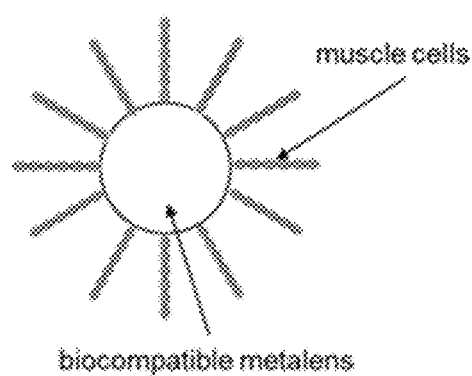
FIG. 4 is a schematic diagram of a tunable bio-metalens based ultrathin IOL for in vivo implantation in accordance with an example embodiment as disclosed herein.

For a tunable biomaterial-based metasurface IOL, a soft and flexible biomaterial-based metasurface lens is constructed and attached to ciliary muscle cells so as to mimic the muscle-actuation of the lens in human eyes when integrated in vivo (see FIG. 4). To this end, the interaction of the muscles cells with a biomaterial-based soft metasurface lens in vitro is studied, and optical tests of muscle cell-actuated metalens triggered by electrical signals, salt solution, or neurotransmitters are conducted.

The normal lens of a human eye is naturally suspended in place by the ciliary zonule (aka zonule of Zinn, Zinn's membrane, ciliary zonule, and suspensory ligaments of the lens) and adhered via a glycoprotein known as fibrillin. The ciliary zonule connects the lens to the ciliary body, which includes the ciliary muscles that actuate the lens. The metalens IOL may be attached to the existing ciliary zonule using surgical glue, such as fibrin glue. Alternatively, or in combination, using an ultrafast laser, pulses of laser light may be used to weld the existing glycoprotein fibrillin contained in the ciliary zonule to the metalens IOL. The metalens IOL may also be mechanically secured to the ciliary zonule using a multitude of small hook fasteners (analogous to the haptics in IOLs).

Figure 5:
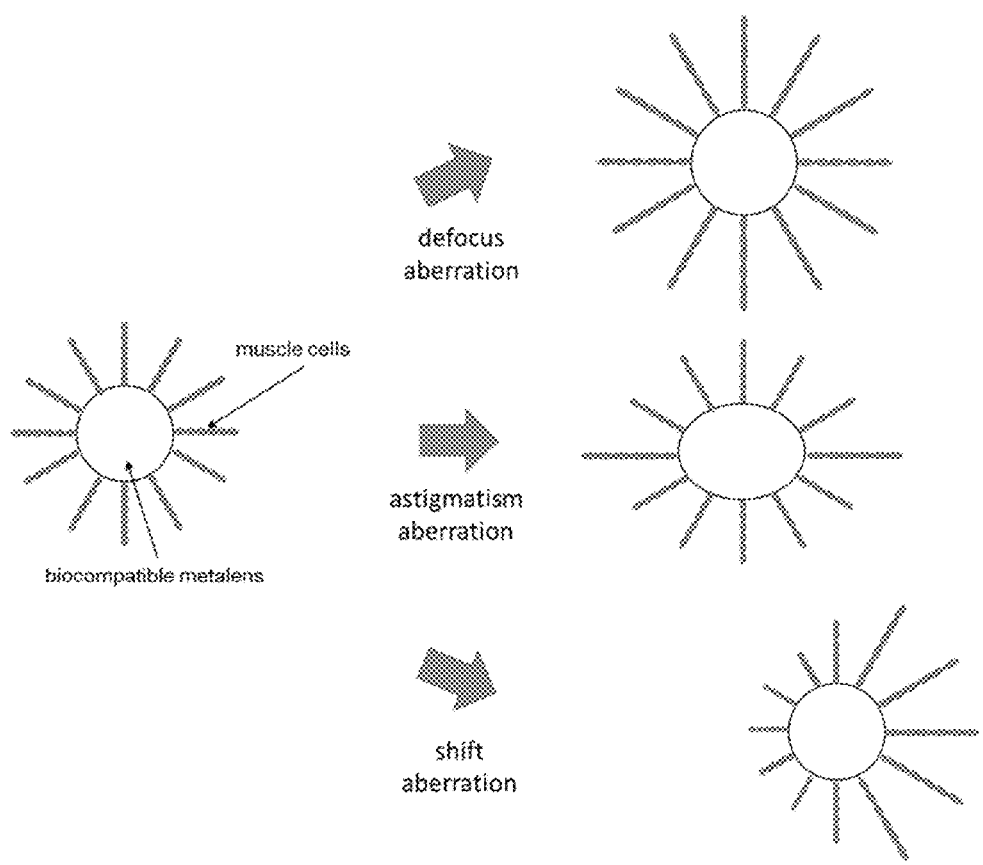
FIG. 5 is an illustration of focal length, astigmatism, and shift of a biomaterial-based metalens being tuned by pushing and/or pulling the connecting muscle cells in accordance with various embodiments disclosed herein.
Figure 6:
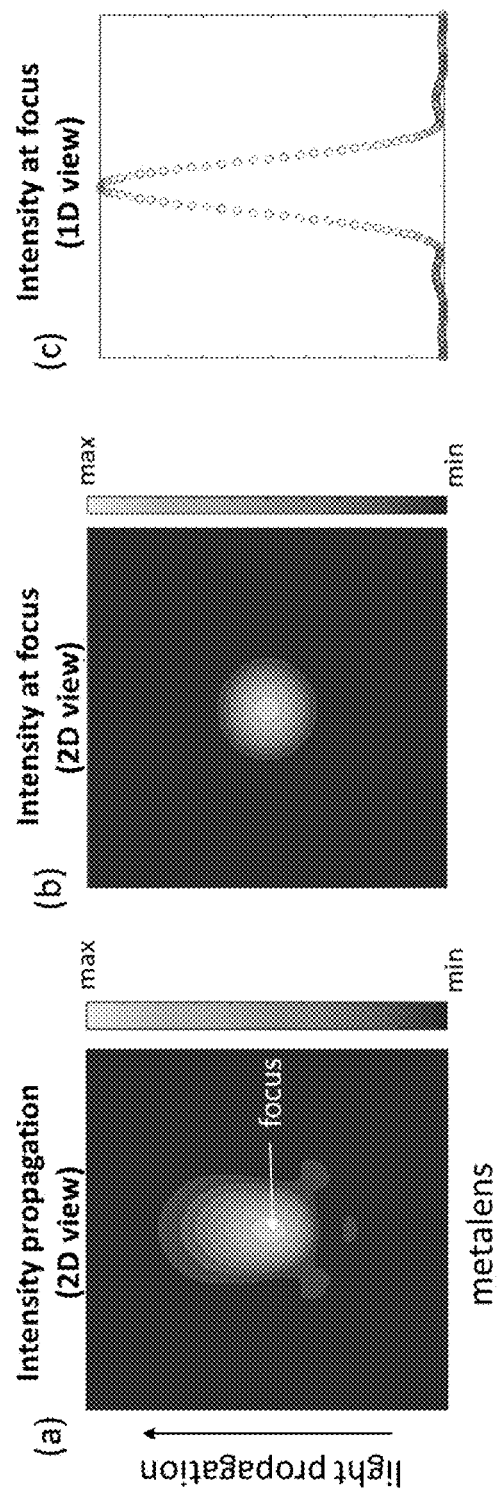
FIG. 6 is a characterisation of the light-focusing properties of a biomaterial-based metalens in accordance with various embodiments disclosed herein. (a) Light intensity along the propagation direction with metalens located at the bottom. (b) Light intensity at focus (2D view). (c) Light intensity at focus (1D view).

Upon integration into a human eye, the ciliary muscles cells maintain or change a shape of the metalens to regulate/vary the focal length, astigmatism, and shift (see FIG. 5) as desired to effect active aberration correction. For example, defocus aberration is corrected by the muscle cells pulling to enlarge the metalens area to increase a focal length, or pushing to reduce the metalens area to decrease a focal length. Astigmatism aberration is corrected by the horizontal and/or vertical muscle cells pushing and/or pulling to make the metalens shape elliptical, so that the focal spot is shifted. Shift aberration is corrected by lateral muscle cells (e.g. left or right side muscle cells) pushing and/or pulling to shift the metalens position in the plane, so that the focal spot is shifted. The metasurface IOL focuses light (see FIG. 6).

Additives may also be added during the making of the IOL to enable smart functionality in the metasurface, such as the ability to respond to changes in its environment, including changes in the pH, temperature, ionic concentration, electric and magnetic fields, chemicals etc. In various examples, stimuli-responsive co-monomers are incorporated into the backbone of a network or as pendant groups in hydrogel to produce various tunable hydrogels that are responsive to different stimuli:

(i) Temperature-responsive hydrogels: Temperature-responsive hydrogels change their structural properties in response to the temperature of their environment. In one example, an inverse temperature-dependent hydrogel, poly(N-isopropylacrylamide) or pNIPAm, is used. In an inverse temperature-dependent hydrogel, the polymer chains either possess moderately hydrophobic groups or a mixture of hydrophilic and hydrophobic segments. Such a hydrogel contracts when the temperature increases. In other examples, positive temperature-dependent hydrogels, poly(ethylene oxide)-b-poly(propylene oxide)-bpoly(ethylene oxide) (Pluronics®, Tetronics®, poloxamer) or their derivatives thereof are used. In these hydrogels, the polymer networks consist of PAA and PAAm. These hydrogels swell when the temperature increases. Depending on the type of hydrogel used (inverse temperature-dependent or positive temperature-dependent), when there is a temperature change, the temperature-responsive hydrogels undergo a reversible transition from a swollen state to a collapsed state or vice versa, thereby causing the metalenses to expand or shrink. The focal length of the metalenses thus increases or decreases accordingly (refer to Example 2 for the metalens tuning principles). Other temperature-responsive hydrogels that may be used include poly(N,N-diethyl acrylamide) (PDEAM), poly(methylvinylether) (PMVE), poly(N-vinylcaprolactam) (PVC), gellan gum, methylcellulose, hydroxypropyl methylcellulose and chitosan.

(ii) pH-responsive hydrogels: In pH-responsive hydrogels, the hydrophilic networks undergo volume deformations in response to changes in the surrounding pH. pH-sensitive polymers possessing ionizable functional groups which either accept or release protons in response to changes in environmental pH may be used. In one example, poly(acrylic acid) is used. In another example, chitosan is used. When there is an increase in the pH, these hydrogels lose a hydrogen ion, resulting in an osmotic pressure increase. Because of osmotic pressure differences, the hydrogels imbibe water and swell. This causes the metalenses to expand and focal length increases as a result. Other possible pH-responsive hydrogels that may be used include polyacids polymer such as poly(methacrylic acid) (PMAAc), poly(2-ethyl acrylic acid) (PEAAc) and polybasis polymer such as poly(N,N-dimethylaminoethyl methacrylate) (PDMAEMA), poly(N,N-diethyl aminoethyl methacrylate) (PDEAEMA) and poly(4-vinylpyridine) (P4VP).

(iii) Light-responsive hydrogels: These include polymeric network possessing light reactive groups such as photochromic moieties. Upon light irradiation (e.g. visible, near-infrared or ultraviolet light irradiation), these hydrogels change their physical and/or chemical properties, including elasticity, viscosity, shape and swelling degree. For example, light-sensitive chromophores such as azobenzenes or immobilizing photocleavable groups can be added into the hydrogel network so that the hydrogels become sensitive to UV light. Chlorophyllin chromophore can be added into pNIPAm hydrogels so that the hydrogels become sensitive to visible light. Up-conversion nanoparticles can be added into hydrogels so that near-infrared light can be used to trigger the structural change. Upon light irradiation, these light-responsive hydrogels change their physical and/or chemical properties, thereby causing a change in the shape of the metalenses. The focal length and/or focal spot/focal spot size changes as a result (refer to Example 2 for metalens tuning principles).

(iv) Electro-responsive hydrogels: Electro-responsive hydrogels are capable of expansion, contraction, elongation and/or bending under the influence of an electric field depending on the hydrogel shape and its position relative to the electrodes. In general, electrically responsive polymers are conducting polymers. For example, naturally occurring polymers such as hyaluronic acid, chondroitin sulfate and agarose may be used. Synthetic polymers that are (meth)acrylate based and/or are synthesized by crosslinking polyionic chains may also be used. When electrical signals generated by the body, for example, by the human nervous system, these hydrogels expand, contract, elongate and/or bend, thereby causing a change in the shape of the metalenses. The focal length and/or focal spot/focal spot size changes as a result (refer to Example 2 for the metalens tuning principles).

(v) Magnetic-responsive hydrogels: One class of magnetic-responsive hydrogels can transform electromagnetic energy into heat. This class of magnetic responsive hydrogel is usually associated with thermoresponsive hydrogels. For example, magnetic iron oxide nanoparticles (MIONs), also known as super magnetic iron oxide nanoparticles (SPIONs) may be incorporated into the polymer matrices to produce such a hydrogel. Under the influence of a magnetic field, e.g. an externally applied magnetic field, these hydrogels transform the electromagnetic energy generated into heat and swell. This causes the metalenses to expand and its focal length increases as a result. Another class of magnetic-responsive hydrogels, such as magnetic particles added into a polymer matrix, can cause the metalenses to deform (e.g. stretch in one or more directions) under the influence of an externally applied magnetic field. This leads to a change in the shape of the metalenses. The focal length and/or focal spot/focal spot size changes as a result (refer to Example 2 for the metalens tuning principles).

(vi) Ionic-responsive hydrogels: Ionic-responsive hydrogels undergo relatively large and abrupt physical or chemical changes in response to small external changes in the ion concentration. An example of an ionic-responsive hydrogel is P (DMAEMA-co-acrylic acid) copolymer. When this is a change in the ionic/salt concentration in its environment, the metalenses deform and the focal length and/or focal spot/focal spot size changes as a result (refer to Example 2 for the metalens tuning principles).

(vii) Multi-responsive hydrogels: Multi-responsive hydrogels respond to two or more external stimuli. An example of a dual sensitive hydrogels that may be used is triblock copolymer poly(amidoamine)-poly(ethylene glycol)-poly(amidoamine) (PAA-PEG-PAA) which is formed by conjugating PAA to PEG via Michael addition polymerization.

Special care needs to be taken to prevent bacterial, viral, fungal, parasitic and prion infections of the IOLs. The entire production process of the IOLs is entirely performed in a sterile environment. Further, the IOLs are also rinsed/washed with one of more of multipurpose solutions, including anti-bio formulations such as chlorohexidine, hydrogen peroxide-based solutions, saline and enzymatic protein removers for sterilization.

Advantageously, embodiments of the biomaterial-based metasurface IOL disclosed herein allow for simultaneous focal length tuning, astigmatism and shift correction potentially enabling augmented vision capabilities. Additionally, as various embodiments of the biomaterial-based metasurface lens are ultrathin, they are ideal for microsurgical implantation and allows for high oxygen permeability which are qualities that are important for success as an IOL. It will also be appreciated that the embodiments of the biomaterial-based metasurface IOL disclosed herein can be customised to suit the ocular conditions of various individuals by designing the metalens using highly precise wavefront shaping.

Figure 7:
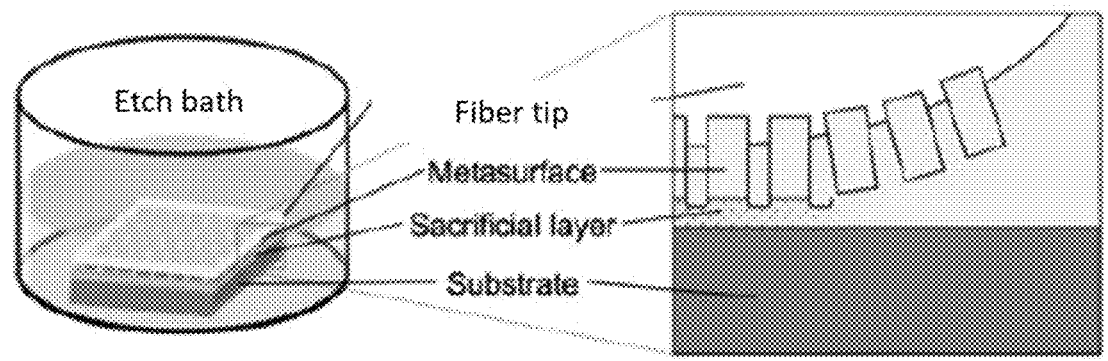
FIG. 7 is a schematic diagram of a method of transferring metalens/metasurface patterns to a fiber tip of an endoscope in accordance with an example embodiment disclosed herein.
Figure 8:
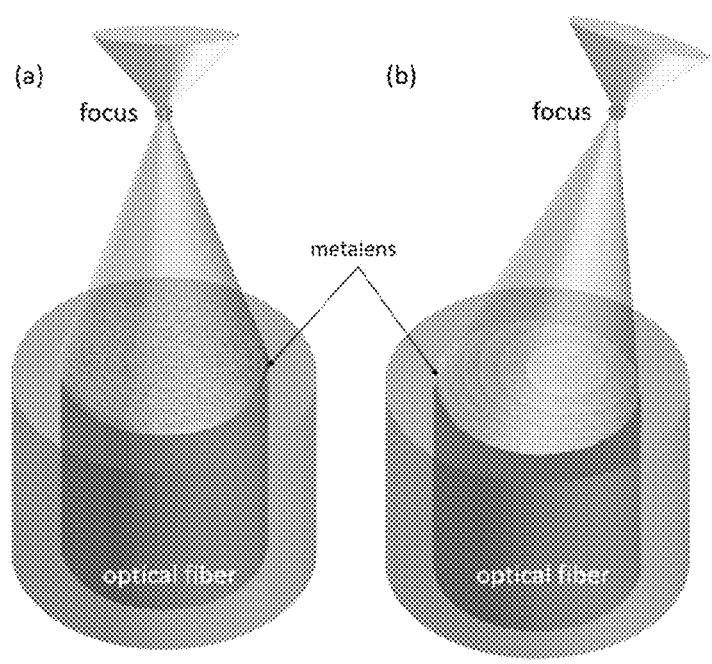
FIG. 8 is a schematic diagram of fiber tip with a biomaterial-based metalens in an endoscope in accordance with an example embodiment disclosed herein. (a) Metalens performs the function of light focusing in a normal-view endoscope. (b) Metalens performs the function of light focusing and light deflecting in a side-view endoscope.

Example 4: Metasurface-Based High-Resolution In Vivo Normal-View and Side-View Endoscopes In accordance with various embodiments disclosed herein, the biomaterial-based metasurface lens may be applied as a lens for use in an endoscope. In such an application, the biomaterial-based metalens is incorporated into an endoscope at a fiber tip. The metalens may be directly written on the fiber tip by focused ion beam. The metalens can also be fabricated separately on a substrate such as a solid wafer or a thin soft membrane and then transferred to the fiber tip. One of the transfer methods is depositing a sacrificial layer atop the substrate layer, and then subsequently removing the sacrificial layer (e.g. via etching) after the metalens/metasurface patterns is/are transferred to the fiber tip (see e.g. FIG. 7). Another transfer method is to directly glue the metalens on the fiber tip. The result is a metasurface-based endoscope that gives high-resolution viewing in normal-view and side-view in vivo (see FIG. 8). The biomaterial-based metalens focuses light in a normal-view endoscope (see FIG. 8 (a)) and in a side-view endoscope, the biomaterial-based metalens focuses and deflects light (see FIG. 8 (b)).

Figure 9:
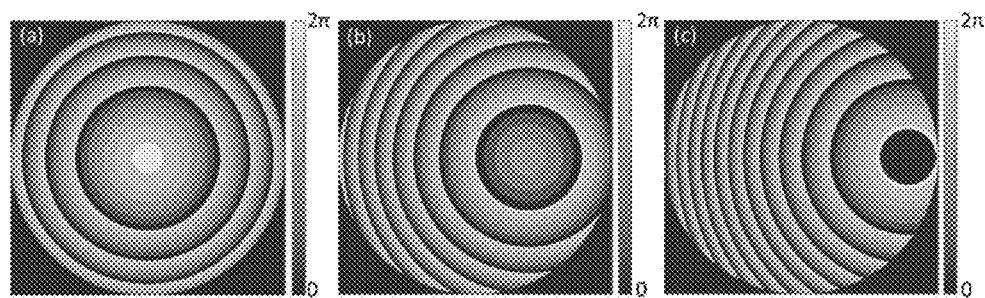
FIG. 9 shows the biomaterial-based metalens phase profile for (a) normal-view endoscope; (b) 5° side-view endoscope and (c) 10° side-view endoscope in accordance with various embodiments disclosed herein.

In the biomaterial metasurface-based endoscope, as the viewing angle increases, there will be more surrounding ring zones which correspond to the linear phase gradient and the centre zone which corresponds to the focusing becomes smaller and is being pushed to the side (see FIG. 9). For light deflection at an angle $\theta_{defl}$ in the x direction, the required phase profile equation is $$\varphi_{defl}(x, \lambda) = \frac{2\pi}{\lambda} \times (x) \times \sin\theta_{defl}$$

For light focusing at a distance f, the required phase profile equation is $$\varphi_{focus}(r, f, \lambda) = -\frac{2\pi}{\lambda} \times \left(\sqrt{r^2 + f^2} - f\right)$$

The final phase profile of the metalens for light focusing at an angle is:

$$\varphi_{total} = \varphi_{defl} + \varphi_{focus}$$

In the above equations, r represents the radial position.

Based on the above equations, the biomaterial-based metasurface is designed to optimise viewing for a normal-view endoscope, a 5° side-view endoscope and 10° side-view endoscope (see FIG. 10). The designs follow the metasurface phase profile equations where $\theta_{defl}$=0.5° and 10° respectively. $\theta_{defl}$ can be any value between 0 and 45°. The design patterns follow a similar trend as the phase patterns in FIG. 9 because of the one-to-one correlation between the metasurface nanostructure and phase.

Figure 11:
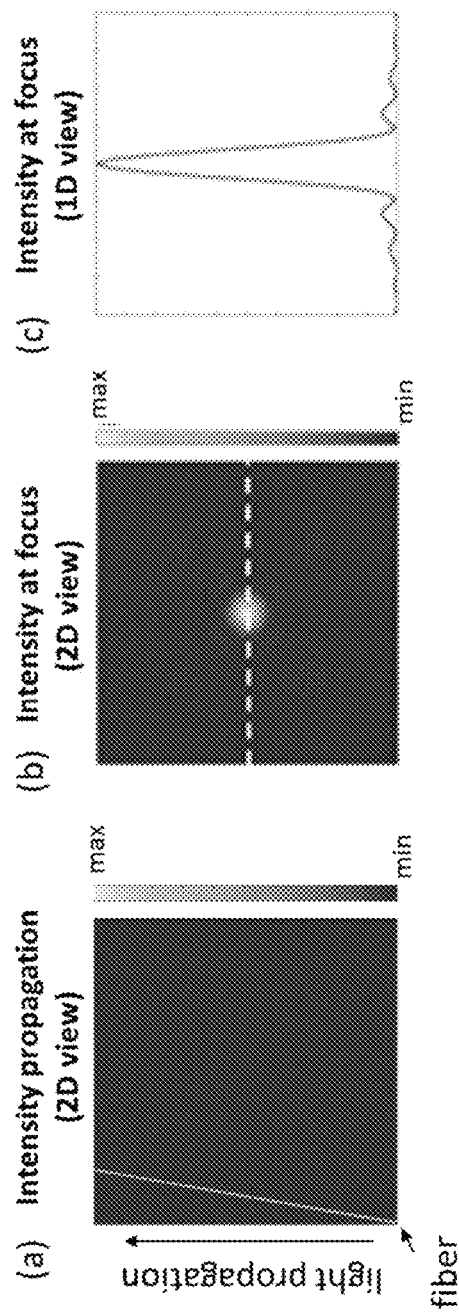
FIG. 11 is a characterisation of output light after being passed through a fiber tip with a biomaterial-based metalens in accordance with various embodiments disclosed herein. (a) Output light is deflected and focused at 10°. (b) Intensity at focus (2D view). (c) Line scan at the focal plane with a diffraction-limited focal spot with an airy function profile.

For 10° side-view endoscopy, after light is being passed through a fibre, the output light is deflected and focused at 10° (see FIG. 11).

Example 5: Implantable Metasurfaces for High-Resolution Deep-Tissue Imaging Through Scattering Media This example describes devices, apparatus, and fabrication process thereof of tunable implantable biomaterial-based metasurfaces comprising a hybrid partially-in vivo and partially-ex vivo optical system for wavefront-corrected high-resolution (sub-micron) deep-tissue (centimeter) imaging through highly scattering media. The system can be used in in vivo brain imaging and in vivo fiber-based endoscopy, although not limited as such.

In the in-vivo part of the system, the setup comprises a series of/multiple foldable bio-metalenses of between 50-100 µm thickness being implanted via needle injection in the media e.g. in a brain media. Each time light passes through a bio-metalens, the total light travelling distance increases. The process repeats until all light is absorbed by the scattering media e.g. tissues. Hence, the total number of metalenses required is determined by the absorption of the scattering media. The number typically ranges from 1-5.

The series of metalenses act as light concentrators to channel light to the deep tissue space. The bio-metalenses collect any highly scattered light and refocus at a distance. The scattered light is refocused until all light is completely absorbed by the scattering media. The total distance light travels in the tissues is equal to the sum of the focal length of all metalenses. In this example, the focal length is in the range of 2 mm to 1 cm (<1 cm). However, depending on the absorption of the scattering media, the ultimate focal length may vary.

Figure 12:
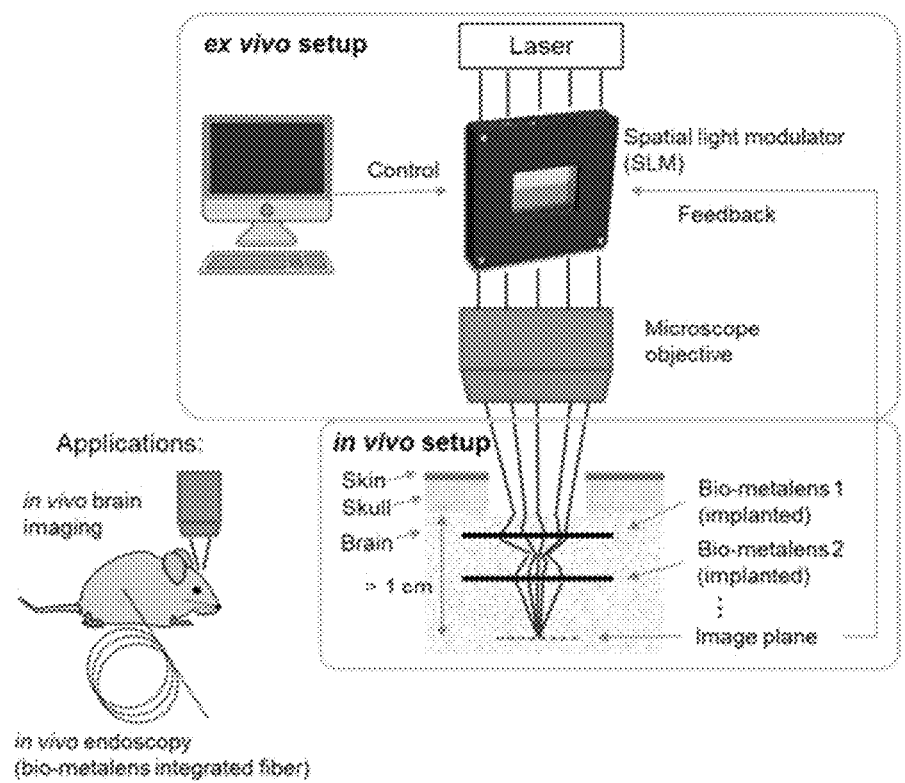
FIG. 12 is a schematic diagram of implantable metasurfaces for high-resolution deep-tissue imaging through scattering media in accordance with an example embodiment disclosed herein.

After injection, the flexible metalens unfolds in the media to focus light on an image plane (see FIG. 12). After light is focused at the image plane, the result of the image processing is directed back through a feedback loop to a spatial light modulator (SLM) in the ex-vivo part of the system. The modulation characteristics of the SLM may be adjusted via a computer or other machines. In the ex-vivo set-up, a laser source is used to direct light to the SLM. The modulated light from the SLM is then directed through a microscope objective before it is being passed through the series of bio-metalenses in the scattering media to focus light on the image plane. The SLM in the system can also be a deformable mirror.

A similar setup may also be implemented for in vivo endoscopy.

The bio-metalens used for deep-tissue imaging in scattering media (see FIG. 13) is composed of polymeric nanopillars (represented by circles in FIG. 13) patterned on a polymeric substrate. Each metalens unit cell is composed of a polymeric nanopillar disposed on a portion of the substrate. The nanopillars may be of the same material as that of the substrate or a different material. Similar structures for the metasurfaces may also be applied for the other applications of IOL and endoscope.

Figure 14:
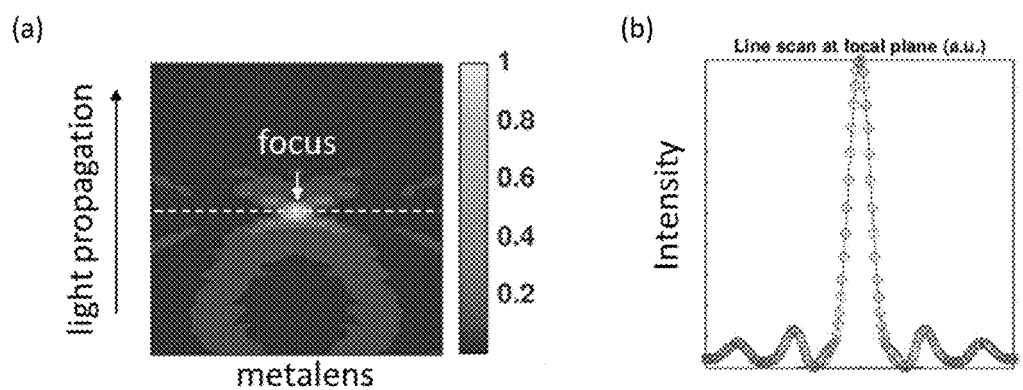
FIG. 14 is a characterisation of output light after being passed through a focusing metalens in accordance with various embodiments disclosed herein. (a) Metalens focuses incident light. (b) Line scan at the focal plane with a diffraction-limited focal spot with an airy function profile.

A whole biomaterial-based metalens is simulated in a water environment to mimic the actual environment in a human body. The light intensity and profile after light is passed through the focusing metalens is shown in FIG. 14.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

Applications

This disclosure describes a class of optical components called metasurfaces that can replace bulky optical devices (e.g., lenses) with the same functionalities. Embodiments of the metasurfaces described herein control the wavefront of light by using arrays of features such as fixed optical phase shifters, amplitude modulators, and/or polarization changing elements. The features of planar optical elements may be patterned on a surface to introduce a desired spatial distribution of optical phases, amplitudes, and/or polarizations of the light. Through the specific design, embodiments of the metasurfaces can achieve various functionalities of optical devices; e.g., lenses, axicons, blazed gratings, vortex plates, wave plates, or a combination of two or more thereof.

Embodiments of the metasurfaces are based on small optical elements that may be spaced less than the distance corresponding to a wavelength of light apart. By reducing the spacing of these metasurface elements, diffraction orders (such as those seen in diffraction gratings or conventional diffractive optical elements) can be suppressed, thus improving performance, and in particular, the efficiency of the metasurface device. Embodiments of the metasurfaces provide a versatile platform for locally modulating the phases, amplitudes, and/or polarizations of an incident wavefront.

Embodiments of the metasurfaces also use biological materials, which capture the dynamic nature of living systems. This approach offers new, exciting mechanisms of tuning as well as a wide range of applications. Embodiments of the biologically tunable metasurfaces open up a new realm of tuning mechanisms, such as chemical environment (pH, humidity, concentration, etc.), biomolecular interactions (e.g. antibody-antigen bonding), light, electric signals, and temperature.

The disclosure also describes devices including tunable and non-tunable metasurface devices based on biomaterials for medical imaging. Embodiments of the devices can react to a variety of external stimuli, e.g. chemical environment, biomolecular interactions (e.g. antibody-antigen binding), light, electric signals, and temperature. Further, embodiments of the devices can be self-healing, self-repairing, and even genetically modified (e.g. optogenetics).

The disclosure also describes the fabrication process for making the biomaterial-based metasurface devices. Embodiments of the devices can be made by templating (nanofabricated templates, e.g. on a wafer), 3D printing, and self-assembly. Materials that are biocompatible, biodegradable, bioresorbable, and/or bioinert are recognised by the disclosure to be especially important for medical applications. Biological materials include polymer-, peptide-, DNA-based materials, living cell sheets, composite biomaterials, etc. as basis for a new materials library for making embodiments of the metasurfaces. In embodiments of the fabrication method, patterned structures are created in these materials using templating (nanofabricated templates, i.e. on a wafer), self-assembly, and 3D printed fabrication routes, with optical functions, including but not limited to adjustable lenses, beam steering gratings, higher-order wavefront aberration correctors, and structural color generators. Embodiments of the metasurface devices are then made tunable in response to one of or multiple of a variety of stimuli, including but not limited to varying pH, temperature, solution concentration, humidity, hydration, electrical signal, and light.

Three applications of metasurface lens (metalens) made of biomaterials are presented herein as examples including: (i) a metasurface-based IOL that is ultrathin (micron), ideal for microsurgical implantation and allows high oxygen permeability for in vivo implantation with simultaneous focal length tuning, astigmatism and shift correction potentially enabling augmented vision capabilities; (ii) a metasurface-based compact in vivo endoscope for normal and side viewing; and (iii) a hybrid partially-in vivo and partially-ex vivo deep-tissue optical imaging system consisting of an in vivo metalens and an ex vivo microscope system with a spatial light modulator for adaptive optics.

The invention claimed is:

1. A concave or convex side-view endoscopic lens for use inside a human or animal body, the lens comprising a metasurface configured to deflect and focus incident light,
   wherein the metasurface is composed of at least one light transmissive biomaterial selected from the group consisting of a hydrogel, a gelatin, a silk fibroin, a polyester, a polysiloxane, a polyacrylate, an acrylate and derivatives thereof, and
   wherein the metasurface comprises patterned nanostructures disposed on a substrate such that the metasurface has a phase profile φ(total) that is defined by the following formulae:

$$\varphi_{total} = \varphi_{defl} + \varphi_{focus}$$

$$\varphi_{defl}(x, \lambda) = \frac{2\pi}{\lambda} \times (x) \times \sin\theta_{defl}$$

$$\varphi_{focus}(r, f, \lambda) = -\frac{2\pi}{\lambda} \times \left(\sqrt{r^2 + f^2} - f\right)$$

where $\theta_{defl}$ is the angle of incident light deflection in the x direction, r is the radial position, f is the focal length and λ is the wavelength of incident light and the positive or negative sign is applied for diverging or converging lenses, respectively.

2. The lens of claim 1, wherein the lens is substantially devoid of materials that elicit an adverse physiological response.

3. The lens of claim 1, wherein the light transmissive biomaterial has a refractive index that is no less than about 1.33.

4. The lens of claim 1, wherein the polyester comprises one or more monomers selected from the group consisting of glycolic acid, glycolide, D, L-lactide, D-lactide, L-lactide, D, L-lactic acid, D-lactic acid, L-lactic acid, ε-caprolactone, trimethylene carbonate, dioxanone and p-dioxanone.

5. The lens of claim 4, wherein the polyester is selected from the group consisting of poly(lactic-co-glycolic acid), polyglycolide, poly(glycolic acid), poly(ε-caprolactone), poly(DL-lactide-co-ε-caprolactone), poly(DL-lactide), poly(L-lactide), polylactide, poly(lactic acid), poly(lactide-co-glycolide), poly(trimethylene carbonate), polydioxanone and poly-p-dioxanone.

6. The lens of claim 1, wherein the polysiloxane is selected from the group consisting of polydimethylsiloxane and polydimethyldiphenylsiloxane; the polyacrylate is selected from the group consisting of poly(ethyl methacrylate) and poly(ethyl acrylate); and the acrylate is selected from hydroxyethylmethacrylate (HEMA) and 2-phenylethyl methacrylate.

7. The lens of claim 1, wherein the patterned nanostructures and the substrate form a single monolithic piece of material.

8. The lens of claim 1, wherein the nanostructures comprise nanopillars.

9. The lens of claim 1, wherein the lens has a total thickness of from 1 micron to 1000 microns.

10. The lens of claim 1, wherein the lens is configured to change its light modulating properties in response to changes in one or more of: chemical environment, biomolecular interactions, intensity of light, electrical and/or magnetic signals, temperature, tensile stresses, or compressive stresses.

11. The lens of claim 1, wherein the lens is an endoscopic lens that is adapted to be integrated directly onto an optical fiber without an intermediate medium such as a prism for redirecting incident light thereto.

12. A method of making a concave or convex side-view endoscopic lens for use in a human or animal body, the lens comprising a metasurface configured to deflect and focus incident light, the method comprising:
   patterning nanostructures on a surface of a substrate to form a metasurface configured to modulate incident light,
   wherein the nanostructures are composed of a light transmissive biomaterial,
   selected from the group consisting of a hydrogel, a gelatin, a silk fibroin, a polyester, a polysiloxane, a polyacrylate, an acrylate and derivatives thereof, and
   wherein the metasurface comprises patterned nanostructures disposed on a substrate such that the metasurface has a phase profile p (total) that is defined by the following formulae:

$$\varphi_{total} = \varphi_{defl} + \varphi_{focus}$$

$$\varphi_{defl}(x, \lambda) = \frac{2\pi}{\lambda} \times (x) \times \sin\theta_{defl}$$

$$\varphi_{focus}(r, f, \lambda) = -\frac{2\pi}{\lambda} \times \left(\sqrt{r^2 + f^2} - f\right)$$

where $\theta_{defl}$, is the angle of incident light deflection in the x direction, r is the radial position, f is the focal length and X is the wavelength of incident light and the positive or negative sign is applied for diverging or converging lenses, respectively.

13. The method of claim 12, wherein the method is performed under sterile conditions and/or further comprises a step of sterilizing the lens.

* * * * *